United States Patent
Beveridge

(10) Patent No.: US 10,489,905 B2
(45) Date of Patent: Nov. 26, 2019

(54) METHOD AND APPARATUS FOR PRESENTATION OF MEDICAL IMAGES

(71) Applicant: Toshiba Medical Systems Corporation, Otawara-shi (JP)

(72) Inventor: Erin Beveridge, Edinburgh (GB)

(73) Assignee: Canon Medical Systems Corporation, Otawara-shi (JP)

( * ) Notice: Subject to any disclaimer, the term of this patent is extended or adjusted under 35 U.S.C. 154(b) by 188 days.

(21) Appl. No.: 15/656,628

(22) Filed: Jul. 21, 2017

(65) Prior Publication Data
US 2019/0026888 A1  Jan. 24, 2019

(51) Int. Cl.
*G06T 7/00* (2017.01)
*A61B 6/03* (2006.01)
*A61B 6/00* (2006.01)
*G06T 11/00* (2006.01)

(52) U.S. Cl.
CPC ............ *G06T 7/0012* (2013.01); *A61B 6/032* (2013.01); *A61B 6/037* (2013.01); *A61B 6/461* (2013.01); *A61B 6/463* (2013.01); *A61B 6/465* (2013.01); *A61B 6/466* (2013.01); *A61B 6/481* (2013.01); *A61B 6/488* (2013.01); *A61B 6/501* (2013.01); *A61B 6/504* (2013.01); *A61B 6/5217* (2013.01); *A61B 6/545* (2013.01); *G06T 11/008* (2013.01); *G06T 2207/10072* (2013.01); *G06T 2207/30016* (2013.01); *G06T 2207/30101* (2013.01)

(58) Field of Classification Search
CPC combination set(s) only.
See application file for complete search history.

(56) References Cited

U.S. PATENT DOCUMENTS

| 7,525,554 | B2 | 4/2009 | Morita et al. |
| 9,152,760 | B2 | 10/2015 | Sherman et al. |
| 9,401,047 | B2 * | 7/2016 | Bogoni ................ G06T 19/00 |
| 2005/0059876 | A1 * | 3/2005 | Krishnan ............. G06T 7/0012 |
| | | | 600/407 |
| 2005/0168474 | A1 | 8/2005 | Truyen |

(Continued)

OTHER PUBLICATIONS

Mohammad A. Dabbah, et al., "Detection and location of 127 anatomical landmarks in diverse CT datasets," Proc. of SPIE vol. 9034, 2014, 11 pages.

*Primary Examiner* — Anand P Bhatnagar
(74) *Attorney, Agent, or Firm* — Oblon, McClelland, Maier & Neustadt, L.L.P.

(57) ABSTRACT

An apparatus for displaying medical images comprises processing circuitry configured to: obtain a first set of medical imaging data from a first scan of an anatomical region of a subject; obtain a second set of medical imaging data from a second scan; process the first set of medical imaging data to detect at least one pathological feature and to determine at least one property associated with the at least one detected pathological feature; select at least one display rule for the second set of medical imaging data in dependence on the determined at least one property, and display at least one image representative of the second set of medical imaging data in accordance with the selected at least one display rule, such that the at least one displayed image provides a desired view of the at least one pathological feature or an anatomical feature associated with the at least one pathological feature.

18 Claims, 6 Drawing Sheets

(56) References Cited

U.S. PATENT DOCUMENTS

| | | | |
|---|---|---|---|
| 2007/0236491 A1* | 10/2007 | Hundley | A61B 5/055 345/418 |
| 2008/0044069 A1* | 2/2008 | DuGal | G06F 19/321 382/128 |
| 2008/0292194 A1* | 11/2008 | Schmidt | G06T 7/0012 382/217 |
| 2009/0016582 A1* | 1/2009 | Penn | A61B 5/055 382/128 |
| 2009/0100105 A1* | 4/2009 | Mutchler | G09B 23/28 |
| 2009/0136099 A1* | 5/2009 | Boyden | G06T 7/0012 382/128 |
| 2009/0318803 A1* | 12/2009 | Abe | A61B 8/08 600/438 |
| 2010/0128942 A1 | 5/2010 | Licato et al. | |
| 2010/0183211 A1 | 7/2010 | Meetz et al. | |
| 2010/0189317 A1* | 7/2010 | Lehmann | A61B 6/463 382/128 |
| 2012/0130226 A1* | 5/2012 | Huizenga | A61B 5/055 600/411 |
| 2015/0097833 A1 | 4/2015 | Razeto et al. | |
| 2016/0110890 A1 | 4/2016 | Smith | |
| 2018/0025255 A1 | 1/2018 | Poole et al. | |

\* cited by examiner

METHOD AND APPARATUS FOR PRESENTATION OF MEDICAL IMAGES

FIELD

Embodiments described herein relate generally to presenting medical images, for example to an apparatus and method for displaying medical images.

BACKGROUND

A stroke may be an example of a serious life-threatening medical condition and may require urgent medical attention, ischemic stroke is one example of a condition that has a limited time window in which a clinician should make a treatment decision. The sooner a patient receives correct treatment the less damage they may be likely to sustain. In this limited time window, decisions may need to be made quickly if brain tissue is to be saved.

Typically, a non-contrast CT scan (NCCT) may be performed as a first time in stroke diagnosis. The NCCT scan results may be used to exclude hemorrhagic stroke as a cause. The NCCT scan results may be used to exclude conditions that mimic the symptoms of stroke, for example seizure and bran tumor. Conditions that mimic the symptoms of stoke may be described as stroke mimics. The NCCT scan results may be used to identify dense vessels (whist may be indicative of a dot) and/or to identify ischemia.

A subsequent CT angiography (CTA) that combines a CT scan with an injection of a contrast medium may be performed to confirm an initial diagnosis and/or to gain more information to aid a treatment decision.

The CTA scan may allow a review of the NCCT scan. For example, features identified in the NCCT scan may be reviewed in the CTA scan. A number of scenarios may occur CTA review. For example, the CTA review may be used to visualize filling defects in vessels to confirm dense vessels that were seen in the NCCT scan but were considered to be dubious or questionable in the NCCT scan. A search for a blockage may be undertaken, for example to review a vasculature supplying a particular region which is ischemic according to the NCCT. The CTA review may be used to review collateral circulation in potential mechanical thrombectomy candidates. The CTA review may be used to determine recanalization success in follow up treatment.

Some stroke imaging leaders advise a NCCT scan followed by a CTA scan as a minimum level of care acute ischemic stroke.

Recent clinical trials have demonstrated, a positive impact on acute ischemic stroke of endovascular therapy and mechanical therapy. As a result, strode management guidelines have been updated to incorporate endovascular therapy, with an emphasis on the importance of imaging. However, expert reading may not be not guaranteed in all clinical centers and/or at all times of day. For example, an on-call radiologist may not specialize in neurological imaging.

Performing a first and second scan and analysing the results second scan may be time-consuming for a medical practitioner. Given the time-sensitive nature of stroke condition, a length of, time taken to review the scan data may in some circumstances have an impact on a clinical outcome. The level of experience of the medical practitioner performing the scan n arriving at the treatment decision may vary. The urgent nature of the condition may in some circumstances lead to incorrect treatment decisions and/or preventable damage occurring.

BRIEF DESCRIPTION OF DRAWINGS

Embodiments are now described, by way of non-limiting example, and are illustrated in the following figures, in which.

DETAILED DESCRIPTION

Certain embodiments provide an apparatus for displaying medical images, the apparatus comprising processing, circuitry configured to: obtain a first set of medical imaging data from a first scan of an anatomical region of a subject; obtain a second set of medical imaging data from a second scan; process the first set of medical imaging data to detect at least one pathological feature and to determine at least one property associated with the at least one detected pathological feature; select at least one display rule for the second set of medical imaging data in dependence on the determined at least one property, and display at least one image representative of the second set of medical imaging data in accordance with the selected, at least one display rule, such that the at least one displayed image provides a desired view of the at least one pathological feature or an anatomical feature associated with the at least one pathological feature.

Certain embodiments provide a method comprising: obtaining a first set of medical imaging data related to a first scan of en anatomical region of a subject; obtaining a second set of medical imaging data related to a second scan; processing the first set of medical imaging data to detect at least one pathological feature and to determine at least one property associated with the at least one pathological feature; selecting at least one display rule for the second set of medical imaging data in dependence on the determined at least one property, and displaying at least one image representative of the second set of medical imaging data in accordance with the selected at least one display rule, such that the at least one displayed image provides a desired view of the at least one pathological feature or an anatomical feature associated with the at least one pathological feature.

Figure 1:
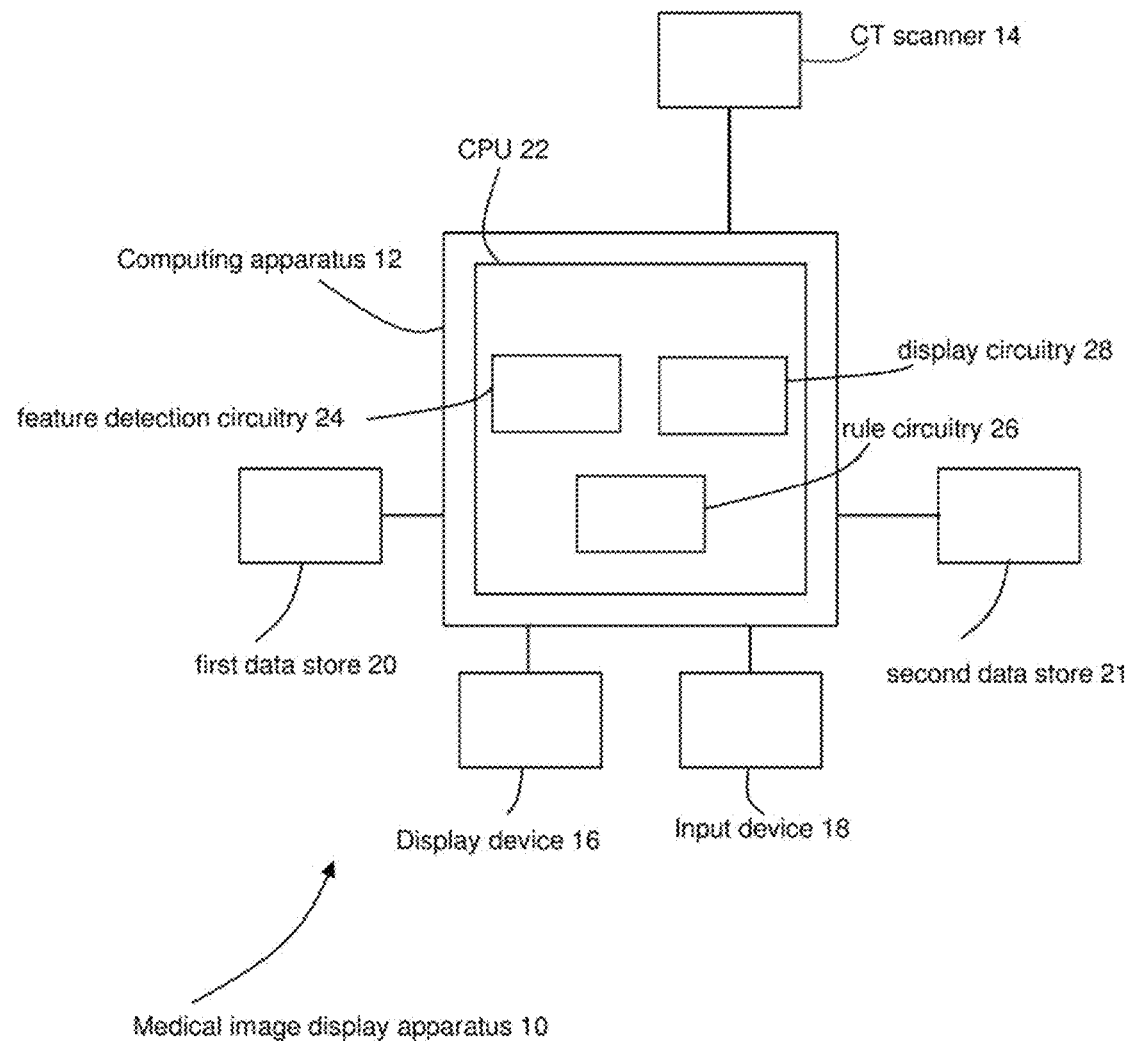
FIG. 1 is a schematic diagram of an apparatus according to are embodiment.

A medical image display apparatus 10 according to an embodiment is illustrated schematically in FIG. 1. The medical image display apparatus 10 is configured to present medical images of a patient or other subject. In other embodiments, the medical image display apparatus 10 may be configured to present any appropriate medical images, where medical may include veterinary.

The medical image display apparatus 10 comprises a computing apparatus 12 which his case is a personal computer (PC) or workstation. The computing apparatus 12 is connected to a display device 16, and an input device or devices 18, such as a computer keyboard and mouse. The display device 16 comprises a screen, in some embodiments, the display device 16 also comprises circuitry configured to receive instructions on now to display images on the screen. The circuitry of the display device 16 may be configured to render images from imaging data locally. In some, embodiments, the display device 16 is a touch screen, which also acts as an input device 18. In some, embodiments, the computing apparatus 12 is a mobile device, for example a smartphone or tablet computer. The computing apparatus 12 may comprise two or more computing devices, which may be connected by a cable or wirelessly.

The computing apparatus 12 is connected to one or more data stores. In the present embodiment, the computing apparatus 12 is connected to a first data store 20 and a second data store 21.

Volumetric imaging data sets related to a first scan are blamed by a CT scanner 14 and stored in the first data store 20. The volumetric imaging data sets are subsequently provided to computing apparatus 12.

Volumetric imaging data sets related to a second scan are obtained by the CT scanner 14 and stored in the second data store 21. The volumetric imaging data sets are subsequently provided to computing apparatus 12. In the present embodiment, the second scan is performed subsequent to performing the first scan and subsequent to administering a contrast medium to the patient. The second scan is a contrast CT scan (CTA scan) and the first scan is a non-contrast CT scan (NCCT scan).

In alternative embodiments, the first and second scans may be obtained using any suitable modality and/or acquisition technique. The CT scanner 14 may be replaced or supplemented by one or more scanners configured to obtain two-dimensional or three-dimensional imaging data in any suitable imaging modality, for example a CT scanner, cone-beam CT scanner, MRI (magnetic resonance imaging) scanner, X-ray scanner, ultrasound scanner, PET scanner (positron emission tomography) or SPECT (single photon emission computed tomography) scanner. The second scan may be acquired using a modality or acquisition technique that is different from a modality or acquisition technique that is used to acquire the first scan.

The computing apparatus 12 is configured to receive medical image data relating to a first scan from first data store 20. The computing apparatus 12 is configured to receive medical imaging data relating to a second scan from second data store 21. In alternative embodiments, the first data store 20 and second data store 21 may be the same storage resource, or may form part of the same storage resource.

In alternative embodiments, the medical image display apparatus 10 receives medical image data and/or medical images from one or more further data stores (not shown) instead of or in addition to first data store 20 and second data store 21. For example, the medical image display apparatus 10 may receive medical image data from one or more remote data stores which may form part of a Picture Archiving and Communication System (PACS) or other information system, for example a laboratory data archive, an Electronic Medical Record (EMR) system, or an Admission Discharge and Transfer (ADT) system.

Computing apparatus provides a processing resource for automatically or semi-automatically processing medical date. Computing apparatus 12 comprises a central processing unit (CPU) 22. The computing apparatus 12 includes feature detection circuitry 24, rule circuitry 26 and display circuitry 28.

In the present embodiment, the circuitries 24, 26, 28 are each implemented in computing apparatus 12 by means of a computer program having computer-readable instructions that are executable to perform the method of the embodiment. However, in other embodiments, the various circuitries may be implemented as one or more ASICs (application specific integrated circuits) or FPGAs (field programmable gate arrays). In the present embodiment, the circuitries 24, 26 and 28 are each implemented as part of the CPU 22. In alternative embodiments, the various circuitries may be implemented separately or form part of two or more CPUs.

Feature detection circuitry 24 is configured to detect one ore pathological features in medical imaging data and to determine at least one property of each detected pathological feature. Rule circuitry 26 is configured to select at least one display rule for displaying medical images, based on, at least in part, the determined properties of detected pathological features. Display circuitry 26 is configured to display a plurality of medical images on display device 16 in accordance with the at least one selected display rule.

The computing apparatus 12 also includes a hard drive and other components of a PC including RAM, ROM, a data bus, an operating system including various device drivers, and hardware devices including a graphics card. Such components are not shown in FIG. 1 for clarity.

The system of FIG. 1 is configured to process first scan data (for example NCCT scan data) to obtain information about abnormalities. The system of FIG. 1 is configured to use the information about the abnormalities to configure a display of second scan data (for example, CTA data) such that the second scan data is displayed using views and viewing, settings that are considered to be most relevant to the abnormalities. For example, the views and viewing settings used to display the CTA data may show an abnormality, or a potential cause of the abnormality.

Figure 2:
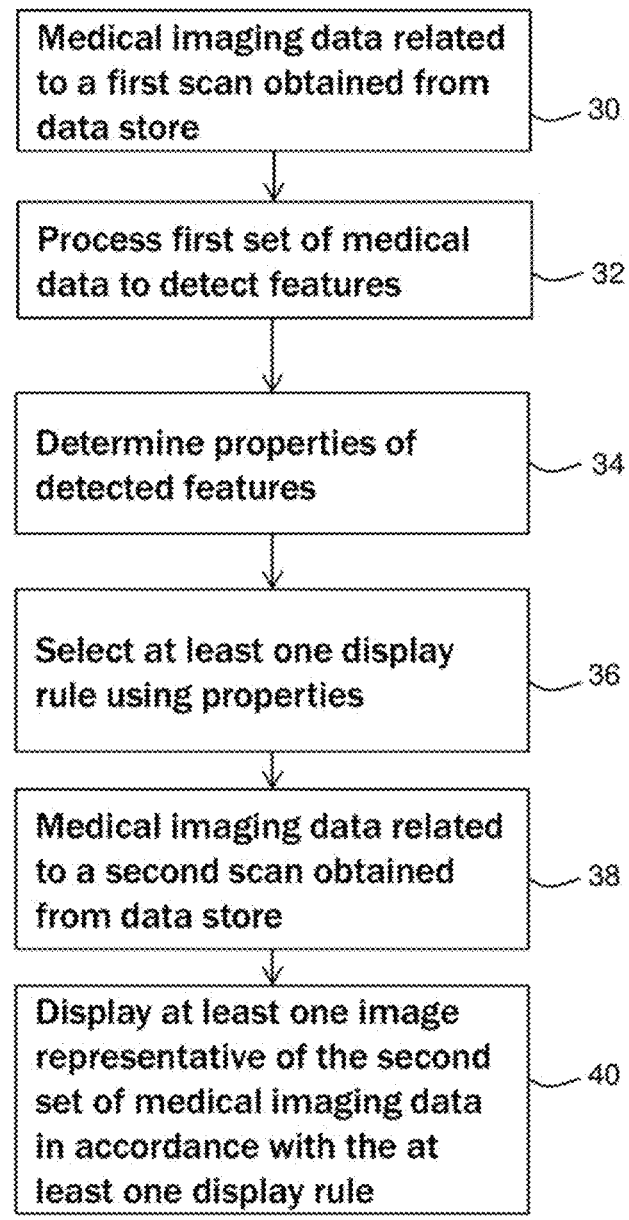
FIG. 2 is a flowchart illustrating in overview a method of displaying medical images.

The system of FIG. 1 is configured to perform series stages as illustrated in overview in the flow chart of FIG. 2.

At stage 30, the feature detection circuitry 24 obtains a first set of medical imaging data from a first data store 20. The medical imaging data obtained from data store 20 relates to a first scan of art anatomical region of a patient. In the present embodiment, the medical imaging data comprises non-contrast CT (NCCT) data from a CT scan of the brain of a patient. It is suspected that the patient has had a stroke. The NCCT data is obtained in order to provide an initial determination of the likelihood that the patient has had a stroke. In other embodiments, the medical imaging data may be representative of a different anatomical region, a different abnormality and/or a different modality. The first scan data may be obtained in order to detect any appropriate disease or condition.

At stage 32 of the flow chart of FIG. 2, the feature detection circuitry 24 detects one or more abnormalities in the obtained first set of medical imaging data. The abnormalities may be referred to as pathological features. The pathological features may include features that are relevant for a stroke condition. For example, each pathological feature may comprise a region of ischemia, dense vessels or infarcts. In other embodiments, different abnormalities may be detected, for example abnormalities relating to a condition other than stroke.

The feature detection 24 may use suitable method of feature detection to detect the pathological features. For example, one or more trained classifiers may be used to detect the pathological features. Different classifiers may be used to detect different pathological features.

In the present embodiment, the feature detection circuitry 24 detects pathological features using a trained detector. The trained detector comprises one or more classifiers that have been trained using a plurality of training data sets. For example, the trained detector may be substantially as described in U.S. patent application Ser. No. 15/216,006.

At stage 34 of the flow chart of FIG. 2, the feature detection circuitry 24 determines at least one property for each detected pathological feature of the medical imaging data. The at least one property may comprise, for example, a classification, an anatomical location, a size, a confidence level, a density, an intensity, a Hounsfield unit value, or an importance.

Determining at least one property of a detected pathological feature may comprise classifying the pathological feature as belonging to a class of features. The pathological feature may be classified as a particular type of abnormality, for example ischemia or dense vessels.

Determining at least one property of a detected feature may comprise determining an anatomical location of the detected feature. An example of anatomical location may be the left perisylvian cortex or the left middle cerebral artery (MCA). The feature detection circuitry 24 may determine the anatomical location using an anatomical atlas, an anatomical detection algorithm, and/or a clinical ontology.

Determining at least one property of a detected pathological feature may comprise assigning a confidence level to the determined pathological feature. For example, the feature detection circuitry 24 may determine that the pathological feature comprises ischemia with an associated confidence level of 90%.

Determining at least one property of the detected feature may comprise determining a size of the detected pathological feature, for example an area or volume of the pathological feature. Determining at least one property of the detected feature may comprise determining an importance of the pathological feature. The importance may be a measure of how serious the pathological feature is. For example, more dangerous and/or urgent pathological features may be given a higher importance. The importance may be dependent on a size of the pathological feature and/or on other properties of the pathological feature.

At stage 36 of the flow chart of FIG. 2, rule circuitry 26 selects at least one display rule based, at least in part, an the one or more determined property associated with the determined pathological features. The or each display rule comprises a rule that is to be applied to the display of data from a second scan of the anatomical region of the patient. The at least one display rule is selected to provide at least one view of the pathological features or of a further anatomical feature that is associated with the pathological features.

In the present embodiment, the rule circuitry 26 selects a set of display rules in dependence on the classification and location of the pathological features that were detected in the first set of medical image data. In other embodiments, the rule circuitry may select one or more display rules using any appropriate property of at least one pathological feature.

The set of display rules is retrieved by the rule circuitry 26 from a store of rules. The store of rules may be stored in memory in the first data store 20, the second data store 21 and/or another memory resource.

In the present embodiment, the display rules are selected from a predetermined collection of display rules. For example, a predetermined collection of display rules may be stored in a look-up table or database or other suitable means configured to be referenced.

In the present embodiment, the set of display rules comprises a DICOM hanging protocol. The hanging protocol defines a set of views and a layout of those views on a display screen. The set of display rules further comprises a set of display parameters for each view. The display parameters may related to at least one of image appearance, image rendering and image data selection. The display parameters may include, for example, size, intensity level, zoom level, anatomical region, viewpoint, intensity window or cine-range.

The display rules are selected by referencing the determined classification and location of the pathological features to a predetermined collection of clinical rules. The clinical rules may comprise information about pathological features and conditions with which the pathological features may be associated. The clinical rules may comprise rules for diagnosis and/or treatment based on the presence or absence of one or pathological features.

The clinical rules may comprise rules for displaying and viewing data in particular clinical scenarios. For example, the clinical rules may comprise a rule that if dense vessel is detected in a NCCT scan, a user must confirm the dense vessel by viewing the same area in a subsequent CTA scan. The clinical rules may comprise a rule that if ischemia is detected in a NCCT scan with no visible cause, the user must determine the cause of the ischemia by viewing vessels that are upstream of the ischemia. The term upstream may refer to how blood is supplied. Vessels that are upstream of a region, may be vessels that, supply blood to that region.

In the present embodiment, the clinical rules relate to stroke and to conditions that may be associated with or relevant to stroke. For example, the clinical rules comprise information about conditions that may be considered to be stroke mimics (for example, seizure or brain tumor). In other embodiments, the clinical rules may relate to any suitable disease or condition.

In the present embodiment, a set of display rules is obtained by referencing the classification and location of pathological features to a set of clinical rules, and obtaining a set of stored display rules for a table of display rules based on clinical rules that apply.

In alternative embodiments, the set of display rules may be selected using a combination of referencing a table and weighting. A different weighting may be applied to different detected pathological features and/or different detected properties. The weighting applied may be based on a determined confidence score or confidence level. In an example implementation, an assigned confidence score is compared to a threshold value. At least one selected display rule may be different if the assigned confidence score is higher or lower than the confidence level threshold. For example, a confidence level for a pathological feature that is lower than the confidence level threshold may be indicative of a need to review the pathological feature in the second scan. In the example implementation, if the confidence level for the pathological feature is below the confidence level threshold, the rules circuitry 26 selects display rules that cause the pathological feature to be displayed.

At stage 38 of the flow chart of FIG. 2, the display circuitry 28 obtains second set of medical imaging data from second data store 21. The medical imaging data relates to a second scan of the patient. The second scan is of substantially the same anatomical region of the patient as the first scan. In the present embodiment, the second scan is a contrast (CTA) scan of the brain of the patient performed subsequent to the first non-contrast (NCCT) scan. In other embodiments, any modality or acquisition technique may be used. The first scan and second scan may be acquired using different modalities or acquisition techniques.

At stage 40 of low chart of FIG. 2, the display circuitry 28 displays images representative of the second set of medical imaging data on the display device 18 in accordance with the selected set of display rules. The images provide views of one or more of the pathological features or n associated anatomical feature of the patient or other subject.

In one example, a region of dense vessel is detected in the first scan data. The set of display rules is such as to display a plurality of images showing the same region of dense vessel in the second scan data. The region of dense vessel in the first scan data may be indicative of a clot. The clot may be diagnosed by viewing the detected region in the second, contrast scan data.

In another example, a first abnormality, for example a region of ischemia, is detected in the first scan data. Occurrence of the first abnormality may typically be linked to a further abnormality in a different anatomical region. For example, if ischemia is detected in the NCCT scan with no visible cause, the cause of the ischemia may be in vessels that are upstream of the reeled of ischemia. The set of display rules may be such as to present a plurality of views of vessels that are upstream of the region of ischemia.

The images displayed by the display circuitry 28 may comprise any suitable views, for example at least one of an anterior circulation view, a posterior circulation view and a collateral circulation view.

The images are displayed in accordance with the set of display rules. The display rules control one or more display parameters for each image. The display parameters may be related to at least one, of image appearance, image rendering, and image data selection. The display rules control size, intensity level, zoom level, anatomical region, viewpoint, intensity window and cine-range of each image. The set of display rules may comprise at least one rule to emphasize or de-emphasize at least one medical image of the plurality of medical images. For example, one image may be made larger or brighter than other images that are displayed at the same time, or may be highlighted in any appropriate manner.

In some embodiments, the medical images are displayed as a sequence. The display rules may determine an ordering of the sequence. For example, the display rules may be such that images that may be considered to be most important are displayed first, images that may be considered to be most important may include, for example, images that may be considered to be most relevant to a diagnosis. The display rules may determine a timing of each image.

The display parameters may be chosen to provide viewing settings that may be considered to be optimal viewing settings. For example, the viewing settings may be considered to be optimal for viewing a pathological feature or anatomical feature that is being viewed. In the present embodiment, the set of display rules comprises is selected automatically by the rule circuitry 26 based on the determined pathological features of the first set of medical data and properties of the determined pathological features.

In further embodiments, the set of display rules may further comprise at least one display rule selected by a user. For example, a user may select one or more views to display. The user may select one or more display parameters, in some embodiments, the user may select one or more display rules in response to viewing the NCCT data. The user may adjust pre-set views, for example views that are provided in accordance with the display rules. The user may adjust any appropriate settings of the views, for example window width/window length (WW/WL), size, or orientation.

In some embodiments, the user may select one or more display rules independently of the NCCT data. For example, the user may select views based on his or her preferences for how data is to be displayed.

In some embodiments, the apparatus 10 comprises a user interface (for example, a user interface displayed on display device 16) which allows a user to indicate an initial diagnosis based on views of the second scan data that are displayed in accordance with the display rules. The user may then confirm a final diagnosis by viewing images displayed in accordance with other display parameters. The user interface may be used to change display parameters of the pre-set views.

Images displayed may include a plurality of views of the substantially same anatomical region of the patient or other subject. Images displayed may include a plurality of different views obtained by differently rendering the second set of medical imaging data. Images displayed may include a plurality of views obtained using different imaging modalities. A most relevant view may be given greater priority (for example, displayed sooner or with a greater size) than other views.

The east one display rule may be selected such that the most relevant view or views of the pathological feature or associated anatomical feature is displayed. For example, views presented may be views that may aid a clinical practitioner to conveniently review first scan images. Views presented may be views that may allow the clinical practitioner to quickly and accurately arrive at a treatment decision. The most relevant stroke view may be presented.

Its some embodiments, the method may also comprise receiving user input via the input device 18 to provide a degree of user control over the displayed at least one image. The user may change display parameters using the input device 18. For example, images may be displayed initially in accordance with the at least one display rule. The user may then adjust the displayed images, for example by changing image parameters.

In some embodiments, the method may include an additional step (not pictured) that comprises displaying clinical information associated with the selection of the display rules. The clinical information may be information that may aid a user, for example a clinical practitioner.

The clinical information may include reasoning as to why the selection of a display rule was made. The clinical formation may include details of why an image is being presented. For example, the clinical information may explain that a particular part of the scan region is being displayed because certain pathological features (for example, dense vessels) have been detected in that part of the scan region.

The clinical information may include instructions, for example, instructions of where to look and what look for. The instructions may be based on the detected features and/or their properties. For example, a clinical practitioner may be directed to look at a region in which a pathological feature has been determined. Clinical information may include a rationale for selection of display parameters. Clinical information may include treatment recommendations, for example a recommendation to perform mechanical thrombectomy. In some embodiments, the displayed clinical information may be based on the stored set of clinical rules.

By displaying images derived from the second scan data in accordance with a set of display rules obtained from the first scan data, a clinician may be directed towards the most relevant information first. In some circumstances, time may be saved by presenting relevant information more quickly than if a standard set of display rules were used (for example, standard display rules that did not take into account the presence of abnormalities). In some circumstances, the display may support an inexperienced user in obtaining a diagnosis.

Figure 3:
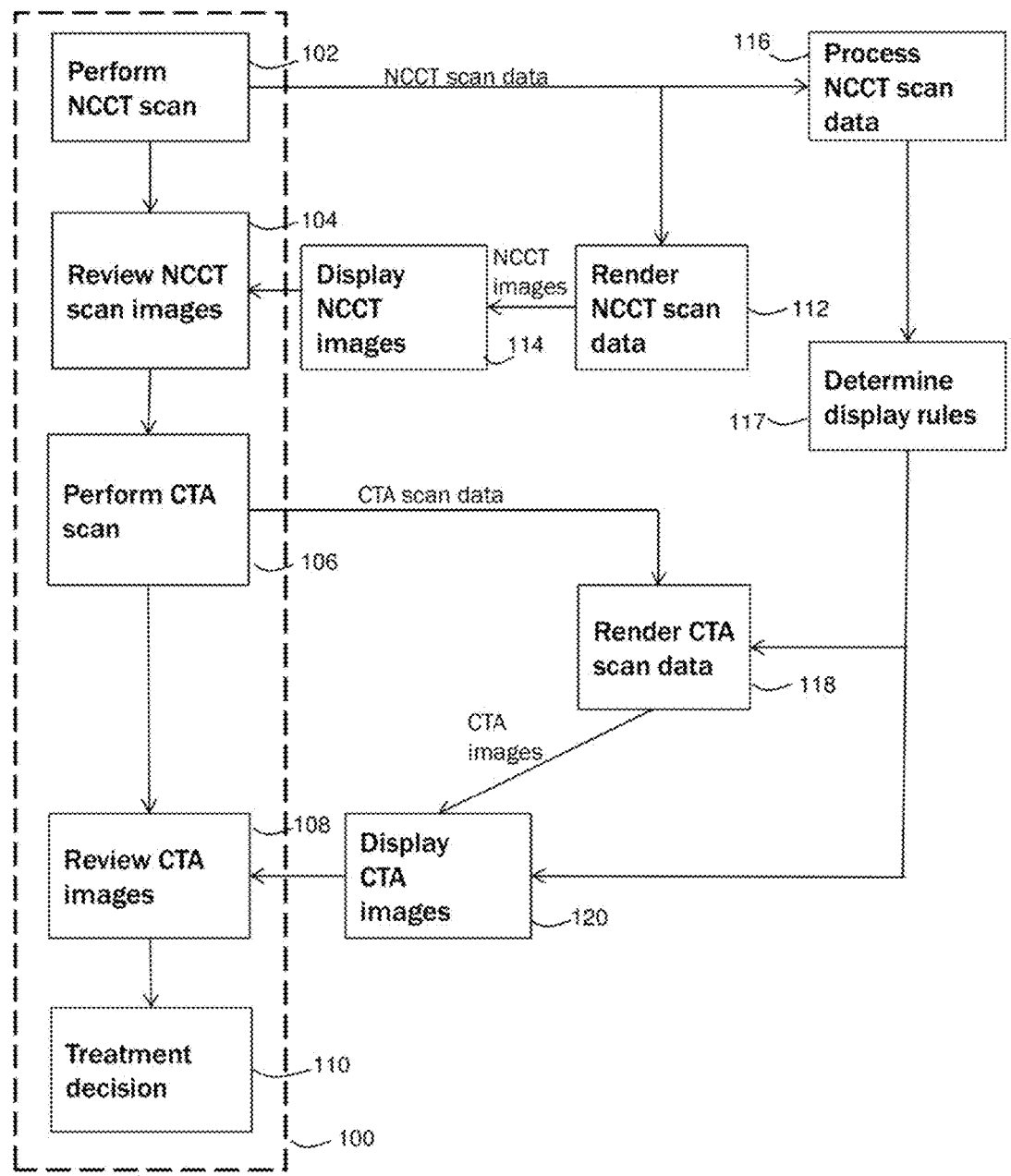
FIG. 3 is a flowchart illustrating in overview a m thud of displaying medical images and a workflow of a medical practitioner.

FIG. 3 shows a flow chart representing integration of an embodiment into a workflow of a medical practitioner, in particular, into stroke diagnosis and/or treatment workflow. Dashed box 100 indicates the workflow of the medical practitioner. The workflow incorporates a first workflow step 102 of performing a first type of scan 102 (a non-contrast CT scan), a second workflow step 104 of reviewing NCCT scan images, a third workflow step 106 of performing a second type of scan 106 (a CTA scan) 108, a fourth workflow step 108 of reviewing CTA images and a fifth workflow step 110 of arriving at a treatment decision. NCCT scan images may usually be reviewed in real-time. If also performed, the CTA scan may usually be performed in the same session as the NCCT scan.

At step 102, the medical practitioner requests for the NCCT scan to be performed. In a case of suspected stroke, the medical practitioner may request the NCCT scan in order to determine whether a stroke has occurred. The NCCT scan is performed using the CT scanner 14. NCCT scan data is collected from the CT scanner 14 by the computing apparatus 12 to be processed and is stored in the first data store 20. Following a stroke incident, it may be important that images representative of the NCCT scan are presented to the medical practitioner as quickly as possible. A first copy of the NCCT scan data is transmitted to the display circuitry 28 and a second copy of the NCCT scan data is transmitted to the feature detection circuitry 24.

At step 112, the display circuitry 28 renders the NCCT scan data to produce medical images representative of the NCCT scan data. At step 114 the NCCT medical images are then displayed by the display circuitry on the display device 16.

Step 114 leads to workflow step 104. The displayed NCCT images permit the medical practitioner to review the NCCT scan data. The medical practitioner makes a preliminary clinical decision based on their review of the NCCT images. For example, the medical practitioner may exclude hemorrhagic stroke an/or exclude stroke mimics (for example, seizure or brain tumor) at this stage. In the case of hemorrhage, administering contrast medium may be harmful, so the medical practitioner may decide not to administer contrast medium if hemontagic stroke is suspected. Following this review of the NCCT scan images, the medical practitioner makes a decision whether to continue with performing a further scan and proceed to step 106 or to take an alternative treatment decision. The medical practitioner may review the NCCT scan images while the patient is still in the scanner.

At step 116, the feature detection circuitry 24 receives the NCCT scan data processes the data to determine one or more pathological features and their properties. In the present embodiment, the processing of the NCCT scan data by the feature detection circuitry 24 is performed automatically and does not depend on the reviewer of the NCCT scan data by the medical practitioner.

With regard to NCCT scan data for stroke conditions, pathological features may include one of dense vessel regions and ischemia regions.

One example of detection of a pathological feature in a first scan is the detection of ischemic signs in non-contrast computed tomography (NCCT). Areas of ischemia and/or infarcts in the brain nay appear in CT images as areas of slightly lowered intensity.

A second example of detection of a pathological feature in a first type of scan is the detection of dense vessels. Dense vessels may be indicative of a thrombus or blood clot. In some circumstances, a thrombus may block a blood vessel, preventing or reducing the flow of blood through that vessel. Thrombus may appear in a CT scan as a region of a vessel having a higher density than other vessel regions. In some circumstances, the signs of thrombus may be referred to as dense vessels. A region of thrombus may show on a CT scan as an abnormally dense vessel structure.

In the case of a thrombus or blood clot, it may be beneficial to offer a clinical practitioner a view of part of the brain that may be responsible for the blood clot or thrombus. The practitioner may then examine where the clot is and see whether the approach route is clear. For example, it can be determined if there is a narrowing in the vessels of the heck that need to be used for access.

In the present embodiment a first classifier is used to detect a first abnormality (for example, thrombus) and a second classifier is used to detect a second abnormality (for example, ischemia). In some embodiments, different classifiers may be used to detect different pathologies, or different classifiers may be used to detect a pathology in different anatomical regions.

In the present embodiment, feature detection circuitry 24 determines a location of each detected feature using an anatomical atlas. The feature detection circuitry 24 receives a set of reference landmarks comprising locations of a plurality of anatomical landmarks in an atlas data set. The locations, are expressed in a coordinate space of the atlas data set.

The atlas data set may comprise a set of reference data, for example a set of volumetric imaging data that is representative of all or part of a human body. The atlas data set may be an imaging data set that is segmented to identify anatomical structures and/or in which anatomical structures are labelled.

An anatomical landmark is usually a well-defined point in an anatomy (for example, the human anatomy). Anatomical landmarks may be defined anatomically, relation to anatomical structures such as bones, vessels or organs. An anatomical landmark may be located in a data set and assigned a set of coordinates in the coordinate frame of that data set. The location of an anatomical landmark may be regarded as a point in coordinate space.

In the present embodiment, the set of reference landmarks comprises landmarks in or near the brain. Examples of such landmarks may include the pineal gland and the base of the pituitary gland.

The feature detection 24 circuitry, aligns the medical imaging data set relating to the NCCT scan to the atlas data set for which the set of reference landmarks is provided. Any suitable alignment method may be used to align the medical imaging data set to the atlas data set based on the landmarks. For example, a rigid or non-rigid registration may be performed. In further embodiments, en alignment method may be performed in which landmarks are not used. In some such embodiments, no reference landmarks may be provided to the feature detection circuitry 24.

The feature detection circuitry 24 detects a plurality of anatomical landmarks in the NCCT scan data set. The anatomical landmarks detected in the NCCT scan data set may correspond to some or all of the reference landmarks that were supplied to the feature detection circuitry 24. For example, the feature detection circuitry 24 may detect the pineal gland and the base of the pituitary gland in the NCCT scan data. The feature detection circuitry 24 determines a location for each of the detected anatomical landmarks in the coordinate space of the NCCT scan data set.

Determining a location of a feature may further comprise mapping the determined location of the detected feature to an ontology to determine a location class. A medical ontology may represent a hierarchy of classifications comprising more than one level of classifications. An example of an ontology is given in FIG. 4.

Figure 4:
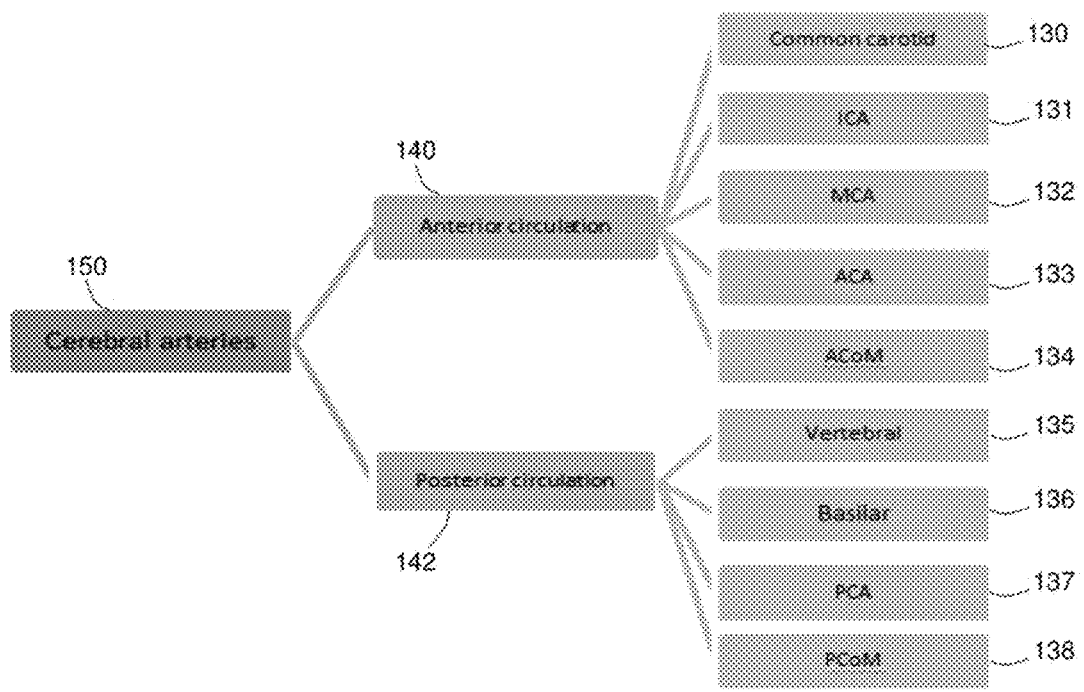
FIG. 4 is schematic diagram of a clinical ontology.

FIG. 4 shows an ontology with a depth of three levels of generalization. On the right hand side FIG. 4 are listed 9 locations of the brain 130 to 138 where features may be presented and detected. The 9 locations are: common carotid 130, internal carotid artery (ICA) 131, middle cerebral artery (MCA) 132, anterior cerebral artery (ACA) 133, anterior communicating artery (ACoM) 134, vertebral artery (Vertebral) 135, basilar artery (Basilar) 136, posterior cerebral artery (PCA) 137 and posterior communicating artery (PCOM) 138. These 9 locations fail into two sub-classes: anterior circulation 140 and posterior circulation 142, as shown in the middle of FIG. 4. Common carotid 130, ICA 131, MCA 132, ACA 133 and AcoM 134 fall into the anterior circulation sub-class 140. Vertebral artery 135, basilar artery 136, PCA 137 and PCoM 138 fall into the posterior circulation sub-class 142. These two sub-classes are sub-classes of a cerebral arteries class 150.

In some embodiments, the feature detection circuitry 24 may determine a location of each detected feature using an anatomical landmark detection method, for example as described in Mohammad A Dabbah, Sean Murphy, Hippolyte Pella, Romain Courbon, Erin Beveridge, Stewart Wiseman, Daniel Wyeth and Ian Poole, 'Detection and location of 127 anatomical landmarks in diverse CT datasets', Proc. SPIE 9034, Medical Imaging 2014: Image Processing, 903415 (Mar. 21, 2014): doi:10.1117/12.2039157. In some embodiments, the location of each detected feature may be determined without using an atlas.

At step 117, rule circuitry 26 determines a set of display rules to be used for displaying the CTA data. The display rules are based on the determined features and/or properties of the determined features in the NCCT scan data. The set of display rules may comprise display rules that are user-determined or predetermined. Different display rules, including different display parameters, may be selected for different detected features. For example, a different window level may be selected on detecting ischemia than for detecting dense vessels.

In some embodiments step 116 of processing NCCT scan data to determine pathological feature, properties of the pathological features and/or step 117 of determining corresponding display rules may be performed at least substantially simultaneously to steps 112 and 114. Display rules may be produced prior to the CTA scan (step 106) being performed.

In alternative embodiments, step 116 may be performed after steps 112 and step 114 (the rendering and display of the NCCT images) are performed. Step 116 may be performed in response to user input via input device 18. For example, step 116 may be performed in the event that a medical practitioner decided to perform a further CTA scan. In further embodiments, step may be automatically performed in response to an event, for example, in response to performing a CTA scan or collection of CTA scan data.

Although in FIG. 3, steps 112 and 116 are presented as separate steps, in some embodiments these steps may be combined. In one embodiment, a set of NCCT data is provided to feature detection circuitry 24. Feature detection circuitry 24 then performs a first processing step to detect pathological features and/or properties of the pathological features in the NCCT sea n data. These detected features and/or properties are stored in a memory resource, for example, first data store 20. The detected pathological features may be used in rendering the NCCT scan data, for example to highlight the detected pathological features for the medical practitioner. In a second processing step (which may follow steps 112, 114 and the review of the NCCT scan images of step 104), the rule circuitry 26 then proceeds to collect the stored features and/or properties and select a set of display rules based on the stored features. By processing the NCCT scan data in stages, features of interest may be highlighted in the NCCT scan images of step 114 and a reduction in data processing may be achieved.

At step 106, a CTA scan is performed using the CT scanner. CTA scan data is collected and stored in the second data store 21. At step 118, the CTA scan data is retrieved by the display circuitry 28. Display rules determined at step 117 are used to render the CTA scan data.

At step 120 the CTA images are displayed on display screen in accordance with the display rules. FIGS. 5a to 5d shows four example views representative of the CTA scan. The views are stroke views which are based on landmarks in the CTA. Stroke views may be views that review specific anatomical and vascular regions of the brain that are relevant to stroke.

A first view (FIG. 5a) is the anterior circulation, the second and third views (FIGS. 5b and 5c) are two views of the posterior circulation and the fourth view (FIG. 5d) is a view of the collateral circulation. The CTA images are displayed according to selected display parameters. The images are aligned to anatomy. The images are slabbed to a selected thickness with window levels set to selected values. The selected values for thickness and window levels may considered to be optimum values for the anatomy that is being viewed and/or for the pathology that is being viewed.

In some embodiments, clinical information may be displayed together with the CTA images. This clinical information may include pertinent information and/or reasoning for displaying the image for the medical practitioner. The clinical information may aid the medical practitioner to focus on the relevant features more quickly and to arrive at a treatment decision. This may be particularly relevant when the medical practitioner is less experienced. By explaining a reason for the specific views shown, the clinical information may help a less experienced clinician to focus on relevant features more quickly.

Clinical information may include treatment recommendations. For example, clinical information may include recommendations to administer a tissue plasminogen activator (tPA), perform no further treatment, or perform mechanical thrombectomy.

The medical practitioner reviews the CTA images at step 108. In some embodiments, the medical practitioner also reviews the accompanying clinical information. Based on the review of the CTA images (and optionally the accompanying clinical information), the medical practitioner proceeds to step 110 which includes arriving at a treatment decision. The medical practitioner decides on a treatment to be performed, or decides that no further treatment is to be performed. Examples of treatments may include administering a tissue plasminogen activator (tPA) or performing mechanical thrombectomy.

In some embodiments, step 104 and 108 also include further steps involving user input via the input device 18. In one embodiment, a user is prompted to input an initial diagnosis or notes at step 104 (when reviewing the NCCT scan images). The user input is then stored. At step 120, the user input is presented together with the CTA scan images for review. Further user input may be received as part of the review of the CTA images.

Figure 6:
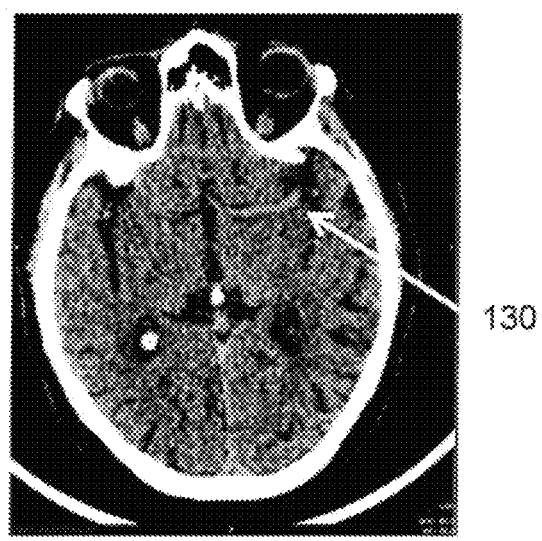
FIG. 6 shows a representation of NCCT scan data.

Several non-limiting examples are now presented of relations between detected abnormalities, location and display rules. Combinations of pathological features and locations may be used to determine display rules;

In a first example, as illustrated in FIG. 6, a first region 130 is detected NCCT scan imaging data. This region is identified as being a region of dense vessels in the location of the middle cerebral artery (MCA). An image of the NCCT scan data is displayed with the first region 130 highlighted. For example, a color overlay may be used to highlight the first region. Information may be displayed indicating that the first region 130 is a region of dense vessel which may indicate a stroke sign, for example a clot. The information may also indicate that the location of the first region 130 is the left MCA.

Figures 5A, 5B, 5C, 5D:
FIGS. 5a to 5d show a plurality of views, with FIG. 5a showing an anterior circulation view, FIGS. 5b and 5c showing posterior circulation views, and FIG. 5d showing a collateral circulation view.

In the example of FIG. 6, no ischemia is detected. The combination of dense vessels in the MCA and no ischemia may be considered to indicate a potential mechanical thrombectomy candidate. For mechanical thrombectomy to be successful, the patient may need to have good collateral circulation. It may be expected that in the CTA scan, the clinician would wish to review the collateral circulation and the anterior circulation. A display rule is selected such that views of the collateral circulation and anterior circulation in the CTA data (as shown in FIGS. 5*a* and 5*d*) are displayed.

In a second example, the NCCT scan data is processed and a region of ischemia is detected in the right lentiform nucleus. No dense vessels are detected ischemia is caused by a blockage. The right lentiform nucleus is supplied by anterior circulation. Therefore the selected display rule is such as to present a view of an associated anatomical region, which is upstream from the ischemia region. In particular, it is known that ischemia in the right lentiform nucleus may be caused by a blockage in the associated region of the anterior circulation. The practitioner wants to search for the blockage. A display rule is selected such as to present an anterior circulation view (as shown in FIG. 5*a*) of the CTA scan to a medical practitioner.

In a third example, the NCCT scan data is processed and region of dense vessel the posterior cerebral artery (PCA) is detected. The PCA forms part of the posterior circulation. The feature is detected with a low certainty value. The certainty is below a threshold value. It is determined that the detection of the region of dense vessel should be reviewed. A display rule associated with the detection of this feature in this location below a certainty threshold is such as to present the two posterior circulation views (as shown in FIGS. 5*b* and 5*c*) to the medical practitioner for review.

The method and system of FIGS. 1 to 3 may sped up review of the CTA scan. The method and system of FIGS. 1 to 3 may aid less experienced physicians to make timely treatment decisions. The method and system may allow a faster review of the intracranial vasculature. The method and system may provide an automated tool to facilitate reading of a relevant medical images. Displaying the most relevant views may help with a timely treatment decision.

In some existing systems, a lot of information may be available prior to the review of the CTA scan (since the NCCT scan is acquired first) but the review of the CTA scan may not make use of the information from the NCCT scan. By using the prior information from the NCCT scan as described above with reference to FIG. 2 and FIG. 3, the review of the CTA scan may be faster. Information from the NCCT scan may be leveraged in order to present the most relevant information from the CTA scan to the clinician, which may comprise a most relevant stroke view. The methods of FIG. 2 and FIG. 3 are facilitated by results from algorithms run on the NCCT scan data plus clinical knowledge.

The method of FIG. 2 or FIG. 3 may be implemented in an automated tool to facilitate reading of relevant images. Such an automated tool may support treatment decisions and triage, for example for acute stroke patients. The method of FIG. 2 or FIG. 3 may be integrated into a multi-panel clinical review display, which may for example be referred to as a dashboard or clinical cockpit. The multi-panel clinical review display may assist a medical practitioner by displaying information, including medical images, in a manner than may make the medical practitioners review of the information quicker and/or more accurate.

Although the embodiments described above are in the context of diagnosis of stroke, methods similar to those of FIGS. 2 and 3 may be used in any appropriate disease cases. Any suitable modality or modalities of data may be used, for example CT data, cone-beam CT data, X-ray data, ultrasound data, MR data, PET data or SPECT data. The first and second scans may be scans of any appropriate anatomical region of a patient or other subject. The selection of display rules may be based on any appropriate clinical rules, which may indicate which images should be displayed in particular clinical scenarios.

In some embodiments, a method similar to those of FIGS. 2 and 3 above is used in a CT polytrauma workflow. A polytrauma workflow may be workflow that is used if a patient has been subjected to multiple traumatic injuries.

A patient may receive a whole body non-contrast CT scan followed by one or more contrast CT scans. Findings from the NCCT scan may influence an order in which various regions and/or views of the contrast enhanced scan or scans may be read.

Rule circuitry may determine at least one display rule in dependence on the NCCT scan. The at least one display rule may comprise a display order.

In one embodiment, feature detection circuitry detects a plurality of abnormalities in the whole body NCCT scan. The abnormalities may comprise abnormalities in different parts of the body. The feature detection circuitry ranks the abnormalities according to seriousness. The rule circuitry determines a set of display rules. The set of display rules causes different regions and/or views of the CTA scan to be ordered according to the ranking determined by the feature detection circuitry. The most serious abnormality (for example, the most serious trauma) may be displayed first. The different regions and/or views may be displayed in order of importance.

Certain embodiments provide a medical imaging method for stroke diagnosis, comprising receiving a non-contrast CT scan of part of a patients brain; receiving a contrasted (CTA) scan of substantially the same part of the patient's brain; processing the non-contrast CT scan to detect at least one pathological feature of relevance to stroke; determining a location and a type for each detected feature; referencing a set of clinical rules to determine, for each detected feature, an optimal set of display parameters for displaying the contrasted (CTA) scan; and displaying the contrasted (CTA) scan to a user according to the optimal display parameters.

A type of the detected pathological feature may be a region of ischemia, or a dense vessel (e.g. due to thrombus). The location of the detected feature may be determined using, at least one of an anatomical atlas and a clinical ontology.

The set of clinical rules may include one of: if dense vessel was detected in CT, the user must confirm by visualizing same area in CTA; if ischemia was detect CT but with no visible cause, the user must determine cause by visualizing vessels upstream of ischemia in CTA.

The optimal set of display parameters may include at least one of an anatomical region, an orientation, a slab thickness, a cine range, a viewpoint, an intensity window, an intensity level, and a zoom level.

The optimal set of display parameters may be determined using, anatomic allocations determined through a registration, an anatomical atlas or a process of anatomical landmark detection in either or both of the CT and CTA scans.

Display of the CTA scan according to the optimal display parameters may be given greater priority (e.g. sooner, or using more screen area) than display of the CTA scan according to other display parameters.

There may be provided a user interface allowing a user to indicate an initial diagnosis according to the optimal display parameters prior to confirming a final diagnosis according to other display parameters. A rationale for and purpose of the optimal display parameters be explained to the user.

Whilst particular have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. An apparatus for displaying medical images, the apparatus comprising processing circuitry configured to:
   obtain a first set of medical imaging data from a first scan of an anatomical region of a subject;
   obtain a second set of medical imaging data from a second scan;
   process the first set of medical imaging data to detect at least one pathological feature and to determine at least one property associated with the at least one detected pathological feature;
   select at least one display rule for the second set of medical imaging data in dependence on the determined at least one property, and
   display at least one image representative of the second set of medical imaging data in accordance with the selected at least one display rule, such that the at least one displayed image provides a desired view of the at least one pathological feature or an anatomical feature associated with the at least one pathological feature.

2. An apparatus according to claim 1, wherein the at least one pathological feature is a pathological feature associated with stroke.

3. An apparatus according to claim 1, wherein the at least one pathological feature comprises at least one of: ischemia, dense vessels, infarct.

4. An apparatus according to claim 1, wherein the at least one associated anatomical feature comprises at least one vessel.

5. An apparatus according to claim 1, wherein the second scan is a scan of substantially the same anatomical region as the first scan.

6. An apparatus according to claim 1, wherein the first scan is a non-contrast scan and the second scan is a contrast scan.

7. An apparatus according to claim 1, wherein the first and second scans differ in at least one of: contrast level, modality, type of acquisition.

8. An apparatus according to claim 1, wherein the at least one image comprises a plurality of images that are displayed in a sequence, the at least one display rule comprising an ordering of the images in the sequence.

9. An apparatus according to claim 1, wherein the at least one image comprises a plurality of images displayed substantially simultaneously, and the at least one display rule comprises at least one of a relative positioning and a relative size of each of the plurality of images.

10. An apparatus according to claim 1, wherein the at least one display rule comprises a hanging protocol.

11. An apparatus according to claim 1, wherein the at least one display rule comprises one or more display parameters for the at least one image, wherein the one or more display parameters are related to at least one of: image appearance, image rendering, image data selection.

12. A method according to claim 1, wherein the desired view comprises at least one of an anterior circulation view, a posterior circulation view and a collateral circulation view.

13. A method according to claim 1, wherein the processing of the first set of medical imaging data to detect the at least one pathological feature comprises using at least one trained classifier.

14. A method according to claim 1, wherein the at least one property comprises at least one of: a location, a classification, a size, a confidence level, a density, an intensity, a Hounsfield unit value, an importance.

15. A method according to claim 1, wherein the processing of the first set of medical image data comprises determining a location for at least one pathological feature using at least one of an anatomical atlas, an anatomical landmark detection algorithm, and a clinical ontology.

16. A method according to claim 1, further comprising displaying clinical information comprising at least one of: a reason for selecting at least one display rule, a set of instructions to the clinician, information regarding the at least one pathological feature and/or the at least one property of the at least one pathological feature, a treatment recommendation.

17. A method comprising:
   obtaining a first set of medical imaging data related to a first scan of an anatomical region of a subject;
   obtaining a second set of medical imaging data related to a second scan;

processing the first set of medical imaging data to detect at least one pathological feature and to determine at least one property associated with the at least one pathological feature;

selecting at least one display rule for the second set of medical imaging data in dependence on the determined at least one property, and displaying at least one image representative of the second set of medical imaging data in accordance with the selected at least one display rule, such that the at least one displayed image provides a desired view of the at least one pathological feature or an anatomical feature associated with the at least one pathological feature.

18. A computer program product comprising a non-transitory computer readable medium storing instructions that are executable to perform a method comprising:

obtaining a first set of medical imaging data related to a first scan of an anatomical region of a subject;

obtaining a second set of medical imaging data related to a second scan;

processing the first set of medical imaging data to detect at least one pathological feature and to determine at least one property associated with the at least one pathological feature;

selecting at least one display rule for the second set of medical imaging data in dependence on the determined at least one property, and displaying at least one image representative of the second set of medical imaging data in accordance with the selected at least one display rule, such that the at least one displayed image provides a desired view of the at least one pathological feature or an anatomical feature associated with the at least one pathological feature.

* * * * *